United States Patent [19]

Alexion et al.

[11] Patent Number: 5,852,061

[45] Date of Patent: Dec. 22, 1998

[54] HYDROCARBON SYNTHESIS WITH CRYOGENIC NITROGEN REMOVAL UPSTREAM OF THE SYNGAS GENERATION

[75] Inventors: Dennis G. Alexion, Succasunna; Constantine A. Coulaloglou, Mendham, both of N.J.

[73] Assignee: Exxon Research and Engineering Company, Florham Park, N.J.

[21] Appl. No.: 851,867

[22] Filed: May 6, 1997

[51] Int. Cl.⁶ .................................................. C07C 27/00
[52] U.S. Cl. ................................................................ 518/700
[58] Field of Search ............................................. 518/700

[56] References Cited

U.S. PATENT DOCUMENTS 5,545,674  8/1996  Behrmann et al. ...................... 518/715
5,617,741  4/1997  McNeil et al. ............................ 62/622
5,647,227  7/1997  Lokhandwala ........................... 62/624

Primary Examiner—Paul J. Killos
Assistant Examiner—L. Parsa
Attorney, Agent, or Firm—Jay Simon

[57] ABSTRACT

In a hydrocarbon synthesis process, nitrogen is cryogenically removed from natural gas to produce a synthesis gas feed comprising methane which is substantially free of nitrogen. This feed is converted to a synthesis gas comprising a mixture of $H_2$ and CO which is substantially free of the HCN and $NH_3$ hydrocarbon synthesis catalyst deactivating nitrogen species. This reduces the need for rejuvenating the hydrocarbon synthesis catalyst. During the cryogenic separation, $C_{2+}$ hydrocarbons are separated from the natural gas and all or a portion of the separated $C_2$–$C_4$ hydrocarbons are added to the methane feed before it is converted into syngas, to increase syngas production. All or a portion of the separated $C_2$–$C_3$ hydrocarbons may be removed as LPG.

21 Claims, 1 Drawing Sheet

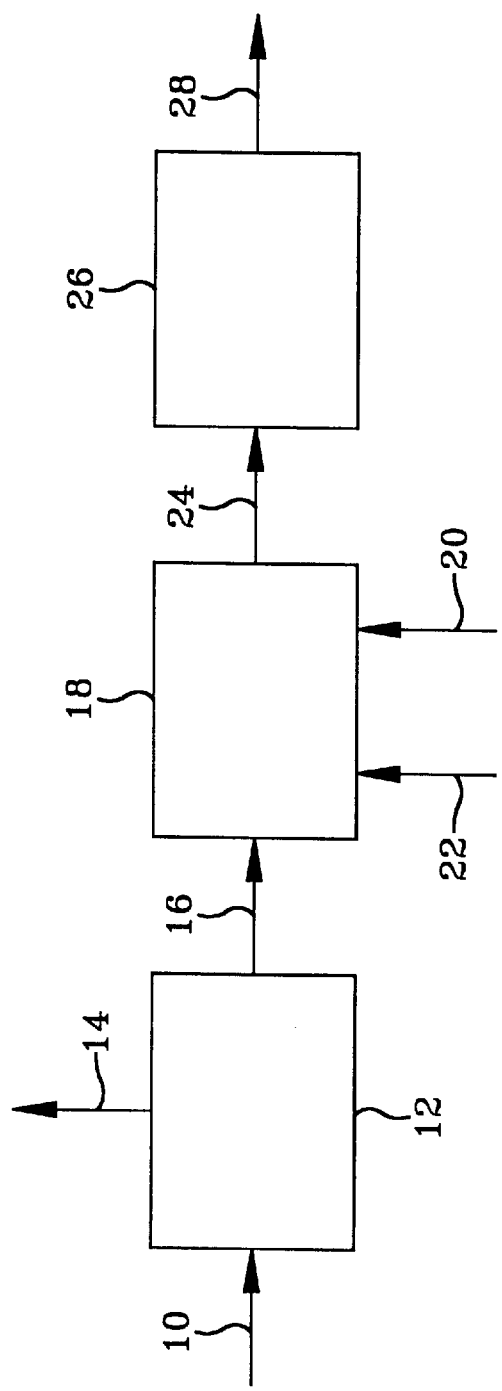

HYDROCARBON SYNTHESIS WITH CRYOGENIC NITROGEN REMOVAL UPSTREAM OF THE SYNGAS GENERATION

BACKGROUND OF THE DISCLOSURE

1. Field of the Invention

The invention relates to a hydrocarbon synthesis process in which nitrogen is removed from natural gas prior to syngas generation. More particularly, the invention relates to a hydrocarbon synthesis process in which nitrogen and $C_{2+}$ hydrocarbons are cryogenically separated from natural gas, with the $C_2$–$C_4$ hydrocarbons added back to the gas to form a nitrogen free, methane rich feed used to produce a syngas free of hydrocarbon synthesis catalyst deactivating nitrogen species.

2. Background of the Invention

Slurry hydrocarbon synthesis (HCS) processes are known. In a slurry HCS process a synthesis gas (syngas) comprising a mixture of $H_2$ and CO is bubbled up as a third phase through a slurry in a reactor in which the slurry liquid comprises hydrocarbon products of the synthesis reaction and the dispersed, suspended solids comprise a suitable Fischer-Tropsch type hydrocarbon synthesis catalyst. Reactors which contain such a three phase slurry are sometimes referred to as "bubble columns", as is disclosed in U.S. Pat. No. 5,348,982. Irrespective of whether the slurry reactor is operated as a dispersed or slumped bed, the mixing conditions in the slurry will typically be somewhere between the two theoretical conditions of plug flow and back mixed. Syngas made from hydrocarbon feedstocks which contain nitrogen (i.e., natural gas) or nitrogen containing compounds (i.e., resids, coal, shale, coke, tar sands, etc.) invariably contains nitrogen species such as HCN and $NH_3$ as a result of the syngas generation process, which contaminate the reactive slurry and rapidly, but reversibly, deactivate the catalyst. Deactivation of such catalysts by these species is reversible and catalytic activity is restored (the catalyst rejuvenated) by contacting the deactivated catalyst with hydrogen. The activity of the HCS catalyst in the reactive slurry may be intermittently or continuously rejuvenated by contacting the slurry with hydrogen or a hydrogen containing gas to form a rejuvenated catalyst slurry as is disclosed, for example, in U.S. Pat. Nos. 5,260,239 and 5,268,344.

In a Fischer-Tropsch HCS process, the catalyst particles slowly lose activity due to deactivating species, such as HCN and $NH_3$, present in the feed gas. Activity loss from these species is reversible and the catalyst is rejuvenated with hydrogen to restore its activity. In a slurry HCS process the catalyst can be rejuvenated in-situ in the slurry by contacting the slurry with a hydrogen containing rejuvenating gas in hollow rejuvenation tubes immersed in the slurry either in the reactor, or in an external rejuvenation vessel as is disclosed, for example, in U.S. Pat. Nos. 5,260,239 and 5,268,344. The need for catalyst rejuvenation is substantially reduced if the syngas doesn't contain these catalyst deactivating nitrogen species. U.S. Pat. No. 5,068,254 discloses removing these catalyst deactivating nitrogen compounds from a syngas feed of $H_2$ and CO by thermal hydrolysis and washing in an aqueous ferrous sulphate solution, to produce a syngas having about 0.1 ppm nitrogen compounds. However, even as little as 0.1 ppm of catalyst deactivating nitrogen compounds in syngas has been found to be unacceptably high in producing rapid catalyst deactivation. For example, as little as 0.1 ppm will result in a catalyst half life of only four days for the case of a supported Co metal catalyst in an HCS slurry.

SUMMARY OF THE INVENTION

The present invention relates to the discovery that cryogenically separating nitrogen from natural gas sent to a synthesis gas (syngas) generating unit results in a syngas relatively free of catalyst deactivating nitrogen species, without the need for hydrolysis and multiple syngas washing steps and the like, downstream of the syngas generation. The cryogenic separation also results in separating $C_{2+}$ hydrocarbons in the gas from the methane. Adding all or a portion of the separated $C_2$–$C_4$ hydrocarbons back into the methane increases syngas production. Thus, in one embodiment the invention relates to a hydrocarbon synthesis (HCS) process which comprises cryogenically separating nitrogen and $C_{2+}$ hydrocarbons from natural gas and adding back all or a portion of the separated $C_2$–$C_4$ hydrocarbons to produce a nitrogen free syngas feed comprising methane and $C_2$–$C_4$ hydrocarbons which is passed into a syngas unit to produce a syngas comprising a mixture of $H_2$ and CO substantially free of catalyst deactivating nitrogen species. This syngas is passed into a hydrocarbon synthesis zone in which it contacts an HCS catalyst to form hydrocarbons, at least a portion of which are liquid at the synthesis conditions. By nitrogen free gas is meant a nitrogen level of less than 100 vppm (volume parts per million), preferably less than 50 vppm, more preferably less than 3 vppm and still more preferably less than 1 vppm. The hydrocarbons formed by the synthesis process are removed from the HCS reactor and upgraded to more valuable products by fractionation and/or conversion. By substantially free of catalyst deactivating nitrogen species is meant less than 50 vppb (volume parts per billion), preferably less than 20 vppb and more preferably less than 10 vppb of the combined total amount of ammonia ($NH_3$) and hydrogen cyanide (HCN) present in the syngas feed being fed into the HCS synthesis zone. Since this process removes the nitrogen from the methane containing gas before it is passed into syngas generating unit, the syngas formed in the unit doesn't contain an unacceptably high level of nitrogenous catalyst deactivating species. This reduces deactivation of the catalyst in the HCS reactor downstream and also the need for removing catalyst deactivating nitrogen species between the syngas generator and the HCS reactor. The hydrocarbon liquids formed by the HCS process in the relative absence of these nitrogen compounds are very pure and easily upgraded by suitable conversion processes into liquid fuel, oil and other products, without the need for severe hydroprocessing (such as hydrotreating) which is commonly used to upgrade similar fractions derived from crude petroleum oil which contain significant amounts of nitrogenous hydrocarbon compounds. Further, since natural gas typically contains in the order of from about 2 to 10 volume % $C_2$–$C_4$ hydrocarbons which are also separated from the methane during the cryogenic separation as part of the $C_{2+}$ hydrocarbons, recovering the $C_2$–$C_4$ hydrocarbons and adding them back to the methane going to the syngas generating unit substantially increases the syngas production. In another embodiment, all or a portion of the separated $C_3$–$C_4$ hydrocarbons are sold separately as LPG as part of an integrated Fischer-Tropsch gas conversion hydrocarbon synthesis and LPG plant. The practice of the invention is useful with any HCS process, including a slurry HCS process. With more specific regard to an HCS process, one embodiment of the invention comprises the steps of:

(a) cryogenically separating nitrogen from a natural gas comprising methane and nitrogen and recovering a gas feed comprising methane having less than 100 vppm of $N_2$;

(b) converting said substantially nitrogen free gas feed to a synthesis gas comprising a mixture of $H_2$ and CO containing no more than 50 vppb of a combined total of HCN and $NH_3$, and (c) reacting said synthesis gas in the presence of a hydrocarbon synthesis catalyst under reaction conditions effective to form hydrocarbons from said syngas.

In further embodiments, $C_{2+}$ hydrocarbons are also separated from the natural gas during the nitrogen separation, from which $C_2-C_4$ hydrocarbons are recovered and all or a portion of the recovered $C_2-C_4$ hydrocarbons added back into the methane feed before it is converted into syngas. The hydrocarbons formed are upgraded to one or more products. In yet another embodiment, all or a portion of the separated $C_3-C_4$ hydrocarbons are sold separately as LPG. In a preferred embodiment most of the hydrocarbon products formed in the reaction zone are either liquid or solid at standard conditions of temperature and pressure. In an embodiment in which the HCS process is a slurry HCS process, the synthesis gas is passed into a hydrocarbon synthesis reaction zone in which it contacts a solid, particulate hydrocarbon synthesis catalyst in a slurry comprising said catalyst, hydrocarbon slurry liquid and gas bubbles, under reaction conditions effective to form hydrocarbons from said syngas, at least a portion of which are liquid at said reaction conditions. The hydrocarbon slurry liquid comprises hydrocarbon reaction products which are liquid at the reaction conditions. At least a portion of the so-formed liquid hydrocarbon products are continuously or intermittently removed from the slurry during the process and are upgraded to more valuable products by one or more conversion operations.

BRIEF DESCRIPTION OF THE DRAWINGS

The FIGURE is a block diagram flow sheet of a hydrocarbon synthesis process according to the invention.

DETAILED DESCRIPTION

In a Fischer-Tropsch HCS process, a syngas comprising a mixture of $H_2$ and CO is catalytically converted into hydrocarbons and preferably liquid hydrocarbons. The mole ratio of the hydrogen to the carbon monoxide may broadly range from about 0.5 to 4, but which is more typically within the range of from about 0.7 to 2.75 and preferably from about 0.7 to 2.5. The stoichiometric mole ratio for a Fischer-Tropsch HCS reaction is 2.0, but there are many reasons for using other than a stoichiometric ratio as those skilled in the art know and a discussion of which is beyond the scope of the present invention. In a slurry HCS process the mole ratio of the $H_2$ to CO is typically about 2.1/1. Slurry HCS process conditions vary somewhat depending on the catalyst and desired products. Typical conditions effective to form hydrocarbons comprising mostly $C_{5+}$ paraffins, (e.g., $C_{5+}-C_{200}$) and preferably $C_{10+}$ paraffins, in a slurry HCS process employing a catalyst comprising a supported cobalt component include, for example, temperatures, pressures and hourly gas space velocities in the range of from about 320°–600° F., 80–600 psi and 100–5,000 V/hr/V, expressed as standard volumes of the gaseous CO and $H_2$ mixture (0° C., 1 atm) per hour per volume of catalyst, respectively. In the practice of the invention, the syngas is formed from natural gas from which nitrogen has been cryogenically removed. Natural gas comprises mostly methane, along with nitrogen, $C_{2+}$ hydrocarbons $C_{2+}$ hydrocarbons and $CO_2$. A typical natural gas comprises, for example, nitrogen in an amount of from about 10–15%, about 2–15% $C_{2+}$ hydrocarbons, of which from about 2–10% are $C_2-C_4$ hydrocarbons, $CO_2$ in an amount of up to about 2% and the remainder methane. The production of syngas from methane by either partial oxidation, steam reforming or a combination thereof is well known as is disclosed, for example, in U.S. Pat. No. 4,888,131. In many cases it is preferred to catalytically partially oxidize and steam reform the methane in a fluid bed syngas generating unit (FBSG) as is disclosed, for example, in U.S. Pat. Nos. 4,888,131 and 5,160,456. The $C_2-C_4$ hydrocarbons in the methane feed are also converted into syngas by reacting with oxygen and/or steam in the syngas unit without adversely effecting syngas production. Irrespective of the source of the methane, nitrogen or nitrogen containing compounds are present in the methane containing gas fed into the syngas generator, some of which are converted into $NH_3$ and HCN during the syngas formation. These will deactivate a Fischer-Tropsch HCS catalyst, particularly those comprising Co as the catalytic metal, and it is difficult and expensive to remove them from the syngas down to a level at which they will not deactivate the HCS catalyst over a reasonable period of time. As the prior art teaches, deactivation by these species is reversible and the catalyst can be rejuvenated by contacting it with hydrogen. This restoration of the catalytic activity of a reversibly deactivated catalyst is referred to as catalyst rejuvenation. Nevertheless, catalyst rejuvenation is costly and catalyst deactivation results in decreased output of the desired hydrocarbon products from the HCS reactor, unless the catalyst rejuvenation is continuous. It has now been found that catalyst deactivation will occur if the combined amount of the $NH_3$ and HCN present in the syngas being fed into an HCS reactor is too high. Therefore, it has been found that the combined amount of these compounds in the syngas should be less than 50 vppb, preferably less than 20 vppb and more preferably less than 10 vppb. It is expensive to remove the $NH_3$ and HCN from the syngas, to such an extent that they are essentially no longer present in amounts that will result in unacceptable catalyst deactivation. Consequently, catalyst rejuvenation with hydrogen or a hydrogen containing gas is required to maintain a reasonable degree of catalyst productivity and selectivity to liquid hydrocarbons. Thus, the removal of $NH_3$ and HCN from the syngas and the requirement of continuous catalyst rejuvenation has been a requirement and a problem. The present invention is a solution to this problem in cryogenically removing nitrogen from the natural gas or other methane source before it is passed into the syngas generator, so that the $NH_3$ and HCN catalyst deactivating species are not present in the syngas in amounts that will result in unacceptable catalyst deactivation. Cryogenic nitrogen removal by cryogenic distillation removes nitrogen from natural gas down to a level less than 100 vppm, preferably less than 50 vppm, more preferably less than 3 vppm and still more preferably no greater than 1 vppm, so that syngas formed from the essentially nitrogen free syngas feed contains less than 50 vppb, preferably less than 20 vppb and more preferably less than 10 vppb of a combined total of the catalyst deactivating HCN and $NH_3$. By cryogenic removal is meant cryogenic distillation and fractionation. Cryogenic distillation and fractionation is used in the processing of natural gas for nitrogen removal to increase the fuel value of the gas for pipelining or LNG applications, helium recovery and LPG ($C_3-C_4$ hydrocarbons) removal. However, cryogenic distillation has not been suggested as a process for providing a nitrogen free methane feed for a syngas generating unit in a Fischer-Tropsch type of hydrocarbon synthesis plant, to provide a syngas with very low levels (if any) of the HCN and $NH_3$ catalyst deactivating species. During the cryogenic distillation the heavier $C_{2+}$ hydrocarbons are separated and fractionated to recover the $C_2$–$C_4$ hydrocarbons, all or a portion of which may be added back to the nitrogen free, methane rich gas to increase syngas production. In another embodiment, all or a portion of the $C_3$–$C_4$ fraction may be recovered and sold as LPG. If present in amount of more than about 2%, $CO_2$ is removed by amine scrubbing and sulfur compounds are also removed from the gas by known processes if present.

In a slurry HCS process, liquid and gaseous hydrocarbon products are formed by contacting a syngas comprising a mixture of $H_2$ and CO with a suitable Fischer-Tropsch reaction type of catalyst comprising, for example, a catalytic metal such as one or more of Fe, Co and Re supported on or composited with titania, silica and the like, dispersed and suspended in a hydrocarbon liquid in a slurry reactor. The syngas is bubbled up into the bottom of the slurry in which it contacts the catalyst particles, to produce the desired liquid hydrocarbon products and, to a lesser extent, less desired gaseous hydrocarbon products. Since the process of the invention removes nitrogen from the natural gas before it is converted into syngas, the syngas is completely free of the $NH_3$ and HCN catalyst deactivating species. Thus, as set forth above, in one embodiment the invention comprises a hydrocarbon synthesis process which comprises cryogenically removing nitrogen from natural gas and passing the nitrogen free gas to a syngas unit to produce a syngas relatively free of catalyst deactivating nitrogen species and which is passed into a hydrocarbon synthesis zone in which it contacts an HCS catalyst in a hydrocarbon slurry liquid, to form liquid hydrocarbons at the synthesis conditions of elevated temperature and pressure, and withdrawing and further processing the so-formed hydrocarbon liquids to form finished products.

The FIGURE is a schematic block diagram of an embodiment of the process of the invention in which a natural gas feed from a gas well is passed, via line 10, into a cryogenic nitrogen rejection and removal unit 12 in which the nitrogen is cryogenically separated and removed from the natural gas and passed out of the unit via line 14 as a stream of nitrogen containing about 14% methane which is blended with fuel gas. While the nitrogen content of natural gas can vary widely, depending on the location from which the gas is taken, a typical and preferred natural gas useful in the process of the invention will comprise about 95% methane and 4% elemental nitrogen, with the small remainder comprising $C_{2+}$ hydrocarbon gasses and $CO_2$. The amount of nitrogen in the natural gas stream doesn't influence the separation of the nitrogen from the methane and the presence of significantly more nitrogen in the natural gas will not change the amount of nitrogen left in the methane after the removal process. For example, irrespective of whether the natural gas has 4 or 14% nitrogen, cryogenic nitrogen removal will still produce a methane gas containing less than 100 vppm, preferably less than 50 vppm, more preferably less than 3 vppm and still more preferably no greater than 1 vppm of nitrogen. If $CO_2$ is present in the natural gas in an amount of greater than about 0.1 mole %, it should be removed from the gas prior to the cryogenic distillation by any suitable means known in the art such as, for example, amine scrubbing, or it will solidify during the cryogenic distillation and plug the unit. Similarly, sulfur, mercury and phosphorous compounds present in the natural gas are also removed by means known in the art prior to the cryogenic nitrogen removal. For example, amine treating is often used to remove sulfur compounds, while mercury and phosphorus compounds are typically removed by activated carbon adsorption. A stream of substantially nitrogen free natural gas comprising methane, along with minor amounts of $C_{2+}$ hydrocarbon gasses, is removed from the cryogenic unit 12 via line 16 and passed into a syngas generating unit 18. The removed nitrogen, along with methane, is removed via line 14 and used as fuel. In this embodiment, syngas unit 18 contains a fluidized bed catalytic reaction zone containing a catalyst comprising nickel on an attrition resistant alumina support methane entering in which the methane containing, nitrogen free natural gas contacts the catalyst in the presence of steam and oxygen, to partially oxidize and reform the nitrogen free methane into a syngas comprising a mixture of $H_2$ and CO which is free of HCS catalyst deactivating, nitrogen species, such as $NH_3$ and HCN. While other processes for producing syngas could be used, FBSG is preferred. Oxygen and steam from suitable sources, such as a cryogenic distillation unit for separating oxygen from air and boiler or HCS product water, are respectively passed into unit 18 via lines 20 and 22. The ratio of the $H_2$ to the CO generated in the syngas unit may broadly range between about 1/1 to 4/1 moles of hydrogen per mole of CO, but more typically nearer to the stoichiometric syngas ratio of 2 moles of $H_2$ for every mole of CO produced. The syngas, free of catalyst deactivating, nitrogen species, is removed from unit 18 via line 24 and passed into a hydrocarbon synthesis reactor 26. In a slurry HCS process, the reactor contains a reactive HCS slurry comprising a particulate hydrocarbon synthesis catalyst and gas bubbles dispersed in a hydrocarbon liquid. The hydrocarbon liquid comprises hydrocarbon products of the hydrocarbon synthesis reaction which are liquid at the synthesis reaction conditions. The bubbles contain unreacted syngas and gas products of the synthesis reaction, of which 50% or more may be water vapor. The syngas is bubbled up into the bottom of the slurry and contacts the catalyst which converts it into liquid and gaseous hydrocarbons. The liquids are withdrawn from the slurry and removed from the reaction zone and reactor via line 28. The gas products of the synthesis reaction are removed from the slurry and reactor as overheads via a gas outlet line (not shown) located at the top of the reactor. Because the syngas entering the reactive HCS slurry does not contain catalyst deactivating nitrogen species, catalyst rejuvenation requirements with a hydrogen containing rejuvenating gas disclosed in the prior art are substantially reduced. Further, the absence of nitrogen compounds in the syngas results in the production of very pure hydrocarbons which are easily upgraded by hydroprocessing and the like, without the need for the more severe hydroprocessing conditions (hydrotreating) that are required for hydrocarbons containing nitrogen compounds. When the HCS catalyst comprises Co or Co and Ru on titania and preferably a titania having a rutile to anatase ratio greater than 1/1, the HCS products are primarily $C_{5+}$ paraffinic hydrocarbons with very little production of aromatics and olefins. HCS catalysts employing Co as a catalytic metal generally produce more of the heavier $C_{20+}$ hydrocarbons and cobalt is a preferred catalytic metal for a slurry hydrocarbon synthesis catalyst.

In an HCS process, liquid and gaseous hydrocarbon products are formed by contacting a syngas comprising a mixture of $H_2$ and CO with a Fischer-Tropsch type of HCS catalyst, under shifting or non-shifting conditions and preferably under non-shifting conditions in which little or no water gas shift reaction occurs, particularly when the catalytic metal comprises Co, Ru or mixture thereof. Suitable Fischer-Tropsch reaction types of catalyst comprise, for example, one or more Group VIII catalytic metals such as Fe, Ni, Co, Ru and Re. In one embodiment the catalyst comprises catalytically effective amounts of Co and one or more of Re, Ru, Fe, Ni, Th, Zr, Hf, U, Mg and La on a suitable inorganic support material, preferably one which comprises one or more refractory metal oxides. Preferred supports for Co containing catalysts comprise titania, particularly when employing a slurry HCS process in which higher molecular weight, primarily paraffinic liquid hydrocarbon products are desired. Useful catalysts and their preparation are known and illustrative, but nonlimiting examples may be found, for example, in U.S. Pat. Nos. 4,568,663; 4,663,305; 4,542,122; 4,621,072 and 5,545,674.

The hydrocarbons produced by an HCS process according to the invention are typically upgraded to more valuable products, by subjecting all or a portion of the $C_{5+}$ hydrocarbons to fractionation and/or conversion. By conversion is meant one or more operations in which the molecular structure of at least a portion of the hydrocarbon is changed and includes both noncatalytic processing (e.g., steam cracking), and catalytic processing (e.g., catalytic cracking) in which a fraction is contacted with a suitable catalyst. If hydrogen is present as a reactant, such process steps are typically referred to as hydroconversion and include, for example, hydroisomerization, hydrocracking, hydrodewaxing, hydrorefining and the more severe hydrorefining referred to as hydrotreating, all conducted at conditions well known in the literature for hydroconversion of hydrocarbon feeds, including hydrocarbon feeds rich in paraffins. Illustrative, but nonlimiting examples of more valuable products formed by conversion include one or more of a synthetic crude oil, liquid fuel, olefins, solvents, lubricating, industrial or medicinal oil, waxy hydrocarbons, nitrogen and oxygen containing compounds, and the like. Liquid fuel includes one or more of motor gasoline, diesel fuel, jet fuel, and kerosene, while lubricating oil includes, for example, automotive, jet, turbine and metal working oils. Industrial oil includes well drilling fluids, agricultural oils, heat transfer fluids and the like.

It is understood that various other embodiments and modifications in the practice of the invention will be apparent to, and can be readily made by, those skilled in the art without departing from the scope and spirit of the invention described above. Accordingly, it is not intended that the scope of the claims appended hereto be limited to the exact description set forth above, but rather that the claims be construed as encompassing all of the features of patentable novelty which reside in the present invention, including all the features and embodiments which would be treated as equivalents thereof by those skilled in the art to which the invention pertains.

What is claimed is:

1. A hydrocarbon synthesis process which comprises the steps of:
   (a) removing $CO_2$ from a natural gas which comprises methane, $N_2$, $CO_2$ and $C_{2+}$ hydrocarbons, to produce a natural gas containing less than 0.1 mole % $CO_2$;
   (b) cryogenically separating said $C_{2+}$ hydrocarbons and $N_2$ from said $CO_2$ reduced gas to produce $C_{2+}$ hydrocarbons and a substantially nitrogen free gas feed gas comprising methane and containing less than 100 vppm of $N_2$;
   (c) converting said substantially nitrogen free gas feed to a synthesis gas comprising a mixture of $H_2$ and CO, and
   (d) reacting said $H_2$ and CO in said synthesis gas in the presence of a hydrocarbon synthesis catalyst under reaction conditions effective to form $C_{5+}$ hydrocarbons.

2. A process according to claim 1 wherein said synthesis gas contains no more than 50 vppb of a combined total of HCN and $NH_3$.

3. A process according to claim 2 wherein said separated $C_{2+}$ hydrocarbons contain $C_2$–$C_4$ hydrocarbons, at least a portion of which are added to said substantially nitrogen free gas feed before it is converted to said synthesis gas.

4. A process according to claim 3 wherein said natural gas also contains one or more of sulfur, mercury and phosphorous compounds which are removed from said gas prior to said cryogenic separation.

5. A process according to claim 4 wherein said substantially nitrogen free gas feed contains less than 50 vppm of $N_2$.

6. A process according to claim 5 wherein said synthesis gas contains no more than 20 vppb of a combined total of HCN and $NH_3$.

7. A process according to claim 4 wherein said $C_{2+}$ hydrocarbons contain $C_3$–$C_4$ hydrocarbons, at least a portion of which are recovered and sold as LPG.

8. A process according to claim 3 wherein at least a portion of the $C_{5+}$ hydrocarbons produced from the synthesis gas is subjected to conversion.

9. A process according to claim 8 wherein the conversion process is non-catalytic.

10. A process according to claim 8 wherein the conversion process is catalytic.

11. A process according to claim 10 wherein hydrogen is present in the catalytic conversion.

12. A process according to claim 11 wherein the catalytic conversion process comprises hydroisomerization.

13. A process according to claim 4 wherein said hydrocarbon synthesis occurs in a slurry which comprises bubbles of said synthesis gas and catalyst in a hydrocarbon slurry liquid which comprises synthesized hydrocarbons which are liquid at said reaction conditions.

14. A process according to claim 13 wherein said substantially nitrogen free gas feed contains less than 50 vppm of $N_2$.

15. A process according to claim 13 wherein said $C_{2+}$ hydrocarbons contain $C_3$–$C_4$ hydrocarbons, at least a portion of which are recovered and sold as LPG.

16. A process according to claim 14 wherein said synthesis gas contains no more than 20 vppb of a combined total of HCN and $NH_3$.

17. A process according to claim 14 wherein said catalyst comprises at least one supported Group VIII metal catalytic component.

18. A process according to claim 17 wherein said support comprises titania.

19. A process according to claim 14 wherein said substantially nitrogen free gas feed contains less than 3 vppm of nitrogen.

20. A process according to claim 19 wherein said synthesis gas contains no more than 20 vppb of a combined amount of HCN and $NH_3$.

21. A process according to claim 4 wherein said $CO_2$ is removed from said natural gas by amine scrubbing prior to said cryogenic separation.

* * * * *